United States Patent [19]

Trofast et al.

[11] Patent Number: 5,637,620
[45] Date of Patent: Jun. 10, 1997

[54] MICRO FORMOTEROL PARTICLES

[75] Inventors: Eva A. Trofast; Lars-Erik Briggner, both of Lund, Sweden

[73] Assignee: Astra Aktiebolag, Sodertalje, Sweden

[21] Appl. No.: 459,660

[22] Filed: Jun. 2, 1995

Related U.S. Application Data

[62] Division of Ser. No. 379,471, Jan. 30, 1995.

[30] Foreign Application Priority Data

Aug. 27, 1993 [SE] Sweden .................................. 9302777

[51] Int. Cl.$^6$ .................................................. A61K 31/16
[52] U.S. Cl. .................................................. 564/630
[58] Field of Search .................................................. 514/630

[56] References Cited

U.S. PATENT DOCUMENTS

| | | | |
|---|---|---|---|
| 3,987,192 | 10/1976 | Wright | 424/304 |
| 3,994,974 | 11/1976 | Muradami et al. | 562/595 |
| 4,405,598 | 9/1983 | Brown et al. | 424/45 |
| 4,476,130 | 10/1984 | Wade | 424/251 |
| 5,376,386 | 12/1994 | Ganderton et al. | 424/499 |

FOREIGN PATENT DOCUMENTS

| | | |
|---|---|---|
| 0436110 | 7/1991 | European Pat. Off. . |
| 0508969 | 10/1992 | European Pat. Off. . |
| 8400294 | 2/1984 | WIPO . |
| 8607547 | 12/1986 | WIPO . |
| 9116882 | 11/1991 | WIPO . |

OTHER PUBLICATIONS

Carstensen et al., "Amorphous–to–Crystalline Transformation of Sucrose," Pharmaceutical Research, vol. 7, No. 12, pp. 1278–1281 (1990).
Orr et al., "The Mixing of Cohesive Powders," The Chemical Engineer, pp. 12–19 (1973).
Otsuka et al., "Effect of Surface Characteristics of Theophylline Anhydrate Powder on Hygroscopic Stability," J. Pharm. Pharmacol., vol. 42, pp. 606–610 (1990).
Ahlneck et al., "The molecular basis of moisture effects on the physical and chemical stability of drugs in the solid state," International Journal of Pharmaceutics, vol. 62, pp. 87–95 (1990).
Makower et al., "Equilibrium Moisture Content and Crystallization of Amorphous Sucrose and Glucose," Agricultural And Food Chemistry, vol. 4, pp. 72–77 (1956).
Palmer et al., "X–Ray Diffractometer and Microscopic Investigation of Crystallization of Amorphous Sucrose," Agricultural And Food Chemistry, vol. 4, pp. 77–81 (1956).
Ahlneck et al., "Chemical and physical stability of drugs in the solid state," Industrial Aspects of Pharmaceutics, edited by Sandell, pp. 81–93 (1973).
ElAmin et al., "Effect of Deactivation of Milled Materials on the Tabletting Properties of Some Crystalline Materials," Swedish Annual Pharmaceutical Congress (1990).
Vidgren et al., "Physical Stability and Inhalation Behavior of Mechanically Micronized and Spray Dried Disodium Cromoglycate in Different Humidities," Acta Pharmaceutica Fennica, vol. 98, pp. 71–78 (1989).

*Primary Examiner*—Theodore J. Criares
*Attorney, Agent, or Firm*—White & Case

[57] ABSTRACT

The present invention relates to a process for providing a stable crystallinic form to a fine-grained substance or a substance mixture, which can be produced, stored and used while maintaining the aerodynamic properties required for inhalation of such a substance or a substance mixture, by a) in case of a substance mixture, preparing a homogenous mixture of the substances;

b) micronizing, direct precipitating or diminishing by any conventional method the substance or substance mixture into a particle size required for inhalation, the particle size being less than 10 μm;

c) optionally preparing a homogenous mixture of the desired substances when each substance has been introduced from stage b) as separate fine-grained particles;

d) conditioning said substance or substance mixture by treatment with a water containing vapour phase in a controlled fashion; and e) drying.

5 Claims, 1 Drawing Sheet

MICRO FORMOTEROL PARTICLES

CROSS REFERENCE TO RELATED APPLICATIONS

This application is a divisional application of Ser. No. 379,471 filed Jan. 30, 1995, pending.

FIELD OF THE INVENTION

The present invention relates to a process for providing a fine-grained substance or substance mixture, which can be produced, stored and used while maintaining the aerodynamic properties required for inhalation of such a substance or substance mixture and which has improved physicochemical properties in the dry state, thereby facilitating the technical handling and significantly increase the medical value of the substance or substance mixture used.

BACKGROUND OF THE INVENTION

There are presently several effective drugs available for the treatment of patients with asthma or other respiratory disorders. It has been recognized that these drugs should be given by the inhaled route whenever possible. The ideal delivery system for inhalable drugs would be a user- and environment-friendly multidose inhaler giving accurate doses of a stable formulation with good aerodynamic behaviour of the particles.

During the past few years, there have been frequent demonstrations of the fact that the appropriate selection of the most suitable crystalline modification significantly can influence the clinical results of a given chemical substance. The chemical and physical stability of a solid in a particular dosage form can be improved by presenting the substance(s) in the appropriate crystal form. The solid state phase transformation of the substance in a dosage form can dramatically alter the pharmaceutical properties of the formulation. The solid state phase of the administered substance(s) can influence such important factors as bioavailability and physicochemical stability (specific surface area, particle size etc). Chemical stability in solid state and hygroscopicity are often closely related to the crystallinity.

Solid state transformations may occur during mechanical processing e.g. micronization. In a micronization process of solids, disruption or activation of the crystalline structure often leads to varying degrees of disorder through the formation of defects or amorphous regions. Such regions are often more sensitive to external effects e.g. moisture. It is necessary to establish the conditions whereby different forms of a substance might be converted to a single stable form, thus eliminating differences in solid state properties and subsequent different physicochemical and pharmaceutical properties.

The increasing production and use of fine powders in the pharmaceutical industry has highlighted the need of reliable methods for assessing their physicochemical and technical handling. Mixing of cohesive powders will be influenced by the interparticulate forces between particles of the same species and also between particles of different species. Since fine powders agglomerate, the mixture will often be inhomogeneous, particularly the minor component will show a skewed distribution. One reason could be that the agglomerates of the minor component are not completely dispersed into their component particles; see further Chem. Eng. (1973), 12–19. Cohesive powders are thus very difficult to mix to a homogenous mixture in an accurate way, especially when one component is present only as a small fraction.

Substances will often be obtained in an amorphous state or a metastable crystalline form when spray drying, freeze drying, rapid solvent quenching or when using controlled precipitation, where both crystalline and amorphous forms can be prepared. The use of an amorphous form or metastable crystalline form is often limited due to its thermodynamic instability. It is therefore a desire to convert the amorphous form or the metastable crystalline form to the more stable crystalline state. For crystalline Substances, a diminution operation step will give amorphous regions of the particle making the particle more sensitive to moisture and chemical degradation. The present invention deals with such physical changes, or more importantly, to anticipate them and the means by which these solid state phenomena can be handled.

The rearrangement or conditioning of a water-soluble substance, amorphous or partly amorphous, using a solvent like ethanol, acetone or the like has been described in Eur. Pat. Appl. EP 508 969 where single compounds have been treated. However, that method is not applicable for some substances containing crystal water, since organic solvents will eliminate the water thereby changing the properties of the substance considerably. It has been understood that water-soluble substances could not be conditioned by water while keeping the particle distribution of a fine-grained substance intact.

REFERENCES

Amorphous-to-Crystalline Transformation of Sucrose, Phar. Res., 7(12), 1278 (1990) by J. T. Carstensen and K. Van Scoik.

Effect of Surface Characteristics of Theophylline Anhydrate Powder on Hygroscopic Stability, J. Pharm. Pharmacol. 42, 606 (1990) by M. Otsuka et al.

Process for conditioning of water-soluble substances, Eur. Pat. Appl. 508969 by J. Trofast et al.

The molecular basis of moisture effect on the physical and chemical stability of drugs in the solid state, Int. J. Pharm. 62(1990), 87–95 by C. Ahlneck and G. Zografi.

BRIEF DESCRIPTION OF THE INVENTION

The object of the invention is to provide a process for a fine-grained substance or substance mixture, which can be produced, stored and used while maintaining the aerodynamic properties required for inhalation of such a substance or substance mixture, by conditioning the substance or substance mixture in a controlled process, thereby facilitating the technical handling and significantly increasing the medical value of the substance or substance mixture formulation used.

DETAILED DESCRIPTION OF THE INVENTION

Figure 1:
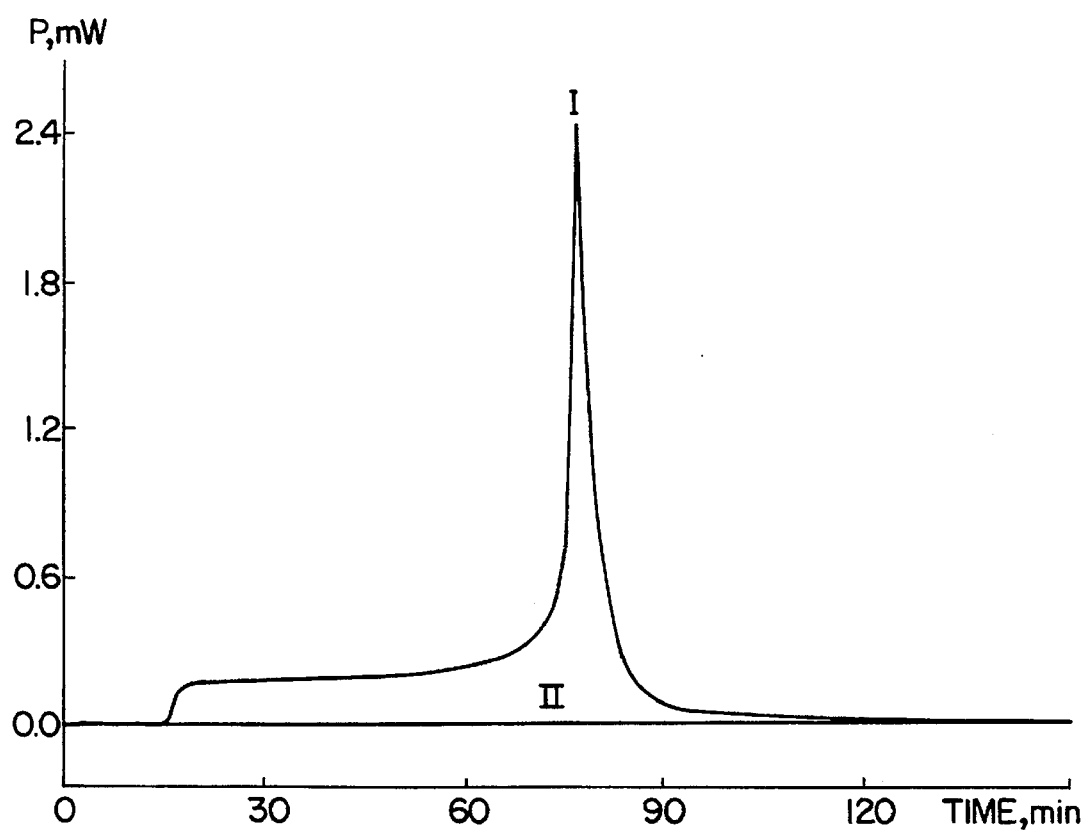

The object of the present invention is to provide a reliable process for providing a stable crystallinic form to a fine-grained substance or a substance mixture, which can be produced, stored and used while maintaining the aerodynamic properties required for inhalation of such a substance or a substance mixture. The process according to the present invention comprises the following steps:

a) in case of a substance mixture, preparing a homogenous mixture of the substances;

b) micronizing, direct precipitating or diminishing by any conventional method the substance or substance mixture into a particle size required for inhalation, the particle size being less than 10 μm;

c) optionally preparing a homogenous mixture of the desired substances when each substance has been introduced from stage b) as separate fine-grained particles;

d) conditioning said substance or substance mixture by treatment with a water containing vapour phase in a controlled fashion; and e) drying.

The conditioning step is carried out by treatment with a water containing vapour phase. Said water containing vapour phase is a water vapour phase with or without any organic solvent vapour present.

The conditioning step is carried out at a temperature/relative humidity combination, which suppresses the glass temperature of substances involved below the process temperature. The glass temperature ($T_g$) is the temperature at which the mobility of an amorphous material undergoes changes from an immobile glassy state to mobile rubbery state (phase transition).

The conditioning is generally carried out at a temperature between 0° and 100° C., preferably between 10° and 50° C. Of practical reasons the conditioning is often performed at ambient temperature. The relative humidity (RH) at which the conditioning is carried out is chosen so that the phase transition occurs, mainly above 35% RH, preferably above 50% RH, and most preferably above 75% RH. The time used is considerably influenced by the batch size, relative humidity and packing etc and may be from minutes to days.

The final formulation may also include different additives, e.g. a substance which enhances the absorption of a pharmacologically active drug in the lung. The enhancers used can be any of a number of compounds which act to enhance absorption through the layer of epithelial cell lining the alveoli of the lung and into the adjacent pulmonary vasculature. Among the substances with known absorption-enhancing properties are surfactants, such as alkali salts of fatty acids, sodium tauro-dihydrofusidate, lecithins, sodium glycocholate, sodium taurocholate, octylglucopyranoside and the like.

Other additives in the formulation may be carriers, diluents, antioxidants, buffer salts and the like, all of which will be treated according to the process of the present invention.

The accuracy and reproducibility of doses are often not sufficient when using very small doses in an inhalation device. Therefore very potent drugs may be diluted with a carrier in order to get an amount of powder sufficient to obtain a reliable and reproducible dose. Such a carrier may be carbohydrates like lactose, glucose, fructose, galactose, trehalose, sucrose, maltose, raffinose, maltitol, melezitose, starch, xylitol, mannitol, myoinositol, and the like and its hydrates, preferably lactose and mannitol, and amino acids such as alanine, betaine and the like.

Coarser particles having a size above 10 µm may also be conditioned using the process according to the present invention.

The present invention may be applied to for example the following pharmacologically active substances:

Formoterol (e.g. as fumarate) and salmeterol (e.g. as xinafoate) are highly selective long-acting $\beta_2$-adrenergic agonists having bronchospasmolytic effect and are effective in the treatment of reversible obstructive lung ailments of various genesis, particularly asthmatic conditions. Salbutamol (e.g. as sulphate), bambuterol (e.g. as hydrochloride), terbutaline (e.g. as sulphate), fenoterol (e.g. as hydrobromide), clenbuterol (e.g. as hydrochloride), procaterol (e.g. as hydrochloride), bitolterol (e.g. as mesylate) and broxaterol are highly selective $\beta_2$-adrenergic agonists and ipratropium bromide is an anticholinergic bronchodilator. Examples of antiinflammatory glucocorticoids are budesonide, (22R)-6α,9α-difluoro-11β,21-dihydroxy-16α,17α-propylmethylenedioxy-4-pregnen-3,20-dione, fluticasone (e.g. as propionate ester), beclomethasone (e.g. as dipropionate ester), tipredane, momethasone and the like. Several of the compounds could be in the form of pharmacologically acceptable esters, salts, solyates, such as hydrates, or solyates of such esters or salts, if any.

The preferred substances to which the invention is to be applied are terbutaline sulphate, salbutamol sulphate, fenoterol hydrobromide, ipratropium bromide, bambuterol hydrochloride, formoterol fumarate and salmeterol xinafoate, and their solvates, especially their hydrates.

The most preferred substance mixture to which the invention is to be applied is formoterol (as formoterol fumarate dihydrate)/lactose (monohydrate), although the same principle may be applied to combinations such as salbutamol (as salbutamol sulphate)/lactose, terbutaline (as terbutaline sulphate)/lactose, ipratropium bromide/lactose, budesonide/lactose, (22R)-6α,9α-difluoro-11β,21-dihydroxy-16α,17α-propylmethhylenedioy-4-pregnen-3,20-dione/mannitol, (22R)-6α,9α-difluoro-11β,21-dihydroxy-16α,17α-propylmethylenedioxy-4-pregnen-3,20-dione/myoinositol and (22R)-6α,9α-difluoro-11β,21-dihydroxy-16α,17α-propylmethylenedioxy-4-pregnen-3,20-dione/lactose. When one of the components is rather insoluble in water, it is possible to use an organic solvent as a conditioning agent for one compound and water vapour as a conditioning agent for the other one in the conditioning step. In that case the conditioning may be carried out in a two step procedure wherein the first step is conditioning with an organic solvent followed by conditioning by water vapour in a second step; or vice versa.

The rearrangement or conditioning of the substance or substance mixture, amorphous or partly amorphous, involve treatment of the substance(s) with a water containing vapour phase in a controlled fashion. This conditioning step is to be performed in a defined environment with controlled and adjustable humidity or a column using inert gas and/or organic solvent vapour containing the required amount of water vapour. The packing of the substance or substance mixture affects the time needed as well as the result of the conditioning. The tendency of caking is affecting the number and size of particles. In case of a substance mixture, it is usually an advantage to mix the substances before the micronizing step in order to ensure a homogenous mixture when using small ratios between the drug substance and the additive.

With the present invention it is possible to condition two or more substances in the same process while the particle distribution is maintained and this is from a technical standpoint a great advantage.

The ratio between the substances in a substance mixture is between 1:1 and 1:1000, preferably between 1:1 and 1:500, and most preferred between 1:1 and 1:200 in the case where one substance is a pharmacologically active substance and the other one is an additive.

The particle size of the fine-grained substances should be identical before and after the conditioning step as measured by different instruments like Malvern Master Sizer, Coulter Counter or a microscope.

It is also of utmost importance that the particles obtained are well-defined in size and distribution as well as have small batch to batch variations in order to obtain agglomerates that will completely disintegrate into its primary particles in the inhaler used.

It is an object of the present invention to provide a reliable process, where the drug formulation of a single drug substance or a combination of a drug substance/additive, preferably formoterol fumarate dihydrate/lactose can be conveniently and reproducibly prepared.

For some material such as formoterol/lactose, where the $T_g$ (the glass transition temperature, the temperature at which the mobility of an amorphous substance undergoes changes from an immobile glassy state to mobile rubbery state) or water sensitivity is markedly different for the drug substance and the additive, the process can be performed in two subsequent steps, i.e. conditioning of one substance at one temperature/RH combination followed by conditioning at a higher temperature/RH for a second substance.

The mixing step is preferably performed before the micronization step in order to ensure the content uniformity or in a single step using a vibratory ball mill as reported by I. Krycer and J. A. Hersey in Int. J. Pharm. 6, 119–129 (1980). It is also possible to mix the substances after micronization or after each substance has been conditioned.

In some instances it has been possible to use infrared spectroscopy in order to study the conversion of an amorphous form or a partly crystalline form into a stable crystalline form. Other methods available include BET gas adsorption, X-ray powder diffraction, isothermal microcalorimetry and differential scanning calorimetry (DSC). We have found that BET gas adsorption and isothermal microcalorimetry being the best methods for distinguishing the different forms of the tested compounds.

When a substance or substance mixture is agglomerated and used as such, a drop of about 70–80% of the respirable particles is found when exposed to high humidity. It has astonishly been found that a drop of only about 25–30% occurs when a substance or substance mixture has been conditioned (at 50% RH for formoterol fumarate dihydrate/lactose mixture) before agglomeration and exposed to high humidity. After further conditioning at 75% RH a drop of only 5–10% of the respirable particles will occur. There is no difference in particle distribution as measured by a Malver instrument before and after conditioning at 75% RH. If the conditioning is performed with the agglomerated product the particle distribution is considerable worse and the formulation useless in an inhalation device.

Experimental procedure

The invention relates to the following procedure:
1. Mixing the drug substance with the additive in a defined ratio.
2. Micronizing the mixture.
3. Conditioning at a temperature/relative humidity combination, which suppresses the glass temperature of substances involved below the process temperature. The glass temperature (Tg) is the temperature at which the mobility of an amorphous material undergoes changes from an immobile glassy state to mobile rubbery state.
4. Drying with dry nitrogen or air, or in vacuum.

EXAMPLES

The invention is further illustrated but not limited by the following examples performed according to the described experimental procedure. Several batches of each substance or substance mixture have been measured. The data represents a comparison of the heat (J/g) given off by non-conditioned and conditioned substances when subjected to a water containing vapour phase. The experiments are performed by using a Thermal Activity Monitor 2277 (Thermometrics AB, Sweden).

EXAMPLE 1

| Salbutamol sulphate (25%)/lactose (75%) | |
| --- | --- |
| Conditioned at relative humidity (RH) | 50–60% RH |
| Non-conditioned substance (J/g) | 5–8 |
| Conditioned substance (J/g) | <0.5 |

EXAMPLE 2

| Ipratropium bromide (6%)/lactose (94%) | |
| --- | --- |
| Conditioned at relative humidity (RH) | 50–60% RH |
| Non-conditioned substance (J/g) | 6–8 |
| Conditioned substance (J/g) | <0.5 |

EXAMPLE 3

| Formoterol fumarate dihydrate | |
| --- | --- |
| Conditioned at relative humidity (RH) | 75% RH |
| Non-conditioned substance (J/g) | 6 |
| Conditioned substance (J/g) | <0.5 |

EXAMPLE 4

| Lactose (see FIG. 1) | |
| --- | --- |
| Conditioned at relative humidity (RH) | 50% RH |
| Non-conditioned substance (J/g) | 10–14 |
| Conditioned substance (J/g) | <0.5 |

EXAMPLE 5

| Melezitose | |
| --- | --- |
| Conditioned at relative humidity (RH) | 50% RH |
| Non-conditioned substance (J/g) | 12 |
| Conditioned substance (J/g) | <0.5 |

EXAMPLE 6

| Formoterol fumarate dihydrate (2%)/lactose (98%) | |
| --- | --- |
| Conditioned at relative humidity (RH) | 50% RH |
| Non-conditioned substance (J/g) | 10–14 |
| Conditioned substance (J/g) | <0.5 |

During a recrystallization a large amount of heat is evolved, and by monitoring the calorimetric signal the sample is checked for any amorphous content. FIG. 1 shows micronised lactose before (I) and after (II) conditioning. Thus, a complete crystallinity has been obtained during the conditioning according to the invention.

We claim:
1. Formoterol fumarate dihydrate having a particle size less than 10 microns, which when subjected to water-containing vapor gives off heat of less than 0.5 J/g.
2. A pharmacologically acceptable mixture comprising formoterol fumarate dihydrate having a particle size of less than 10 microns and an additive, which when subjected to water-containing vapor gives off heat of less than 0.5 J/g.

3. The mixture according to claim 2, wherein the additive has a particle size of less than 10 microns.

4. The mixture according to either claim 2 or claim 3, wherein the additive is lactose.

5. A mixture according to claim 2, wherein the weight ratio of the formoterol fumarate dihydrate to the additive is from 1:1 to 1:200.

* * * * *